United States Patent
Diehm et al.

(10) Patent No.: US 10,031,091 B2
(45) Date of Patent: Jul. 24, 2018

(54) SHIFTING TURN TABLE FOR X-RAY IMAGING MANIPULATOR

(71) Applicant: Avonix Imaging, LLC, Maple Grove, MN (US)

(72) Inventors: Jeffrey Diehm, Columbia Heights, MN (US); Brian Ruether, Zimmerman, MN (US); Joel Ostby, Edina, MN (US)

(73) Assignee: Avonix Imaging, LLC, Maple Grove, MN (US)

( * ) Notice: Subject to any disclaimer, the term of this patent is extended or adjusted under 35 U.S.C. 154(b) by 150 days.

(21) Appl. No.: 15/220,959

(22) Filed: Jul. 27, 2016

(65) Prior Publication Data

US 2018/0031495 A1    Feb. 1, 2018

(51) Int. Cl.
*G01N 23/04* (2018.01)
*G01N 23/046* (2018.01)

(52) U.S. Cl.
CPC ..... *G01N 23/046* (2013.01); *G01N 2223/321* (2013.01); *G01N 2223/419* (2013.01)

(58) Field of Classification Search
CPC ........... G01N 23/046; G01N 2223/321; G01N 2223/419
See application file for complete search history.

(56) References Cited

U.S. PATENT DOCUMENTS

| | | | | |
|---|---|---|---|---|
| 5,023,895 A | * | 6/1991 | McCroskey | G01N 23/046 378/10 |
| 2002/0097831 A1 | * | 7/2002 | Cheng | A61B 6/032 378/20 |
| 2004/0081276 A1 | * | 4/2004 | Roy | G01N 23/046 378/57 |
| 2008/0089466 A1 | * | 4/2008 | Munker | G01N 23/046 378/14 |
| 2011/0188626 A1 | * | 8/2011 | Moriyoshi | G01N 23/046 378/19 |
| 2016/0189403 A1 | * | 6/2016 | Xiao | G01N 23/046 378/4 |

* cited by examiner

*Primary Examiner* — Mark R Gaworecki
(74) *Attorney, Agent, or Firm* — Winthrop & Weinstine, P.A.

(57) ABSTRACT

A component imaging system having at least one x-ray tube and an x-ray detector comprises a rotatable platform positioned between the x-ray tube and the x-ray detector. The rotatable platform is rotatable about a first rotational axis. A turntable is mounted on top of the rotatable platform. The turntable comprises: a stage platform for holding a component having an area of interest, the area of interest having a rotational axis; and a mounting plate rotating with the rotatable platform about the first rotational axis. The stage platform is movable in at least a first direction from a starting position to an imaging position to align the rotational axis of the area of interest with the rotational axis of the rotatable platform.

20 Claims, 12 Drawing Sheets

SHIFTING TURN TABLE FOR X-RAY IMAGING MANIPULATOR

FIELD OF THE INVENTION

The present disclosure relates to novel and advantageous systems and methods for imaging systems, and particularly to systems and methods for positioning or manipulator components within imaging systems.

BACKGROUND OF THE INVENTION

Oftentimes, one or more objects or components may need to be, or are desired to be, internally inspected in order to obtain information regarding the component that is not visually available on an exterior inspection, to identify the internal structure of the component, to view structural fractures or other failures of the component, or to review the inner workings of the component. Components may include parts of products or entire products. One way to inspect components for these and other similar issues is with x-ray computed tomography (CT) scans. For such scans, the component may often be positioned on a rotatable axis or a rotatable platform with a rotatable axis between an x-ray tube and an x-ray detector, where the x-ray tube transmits an x-ray beam against and through the component that is detected by the x-ray detector and converted into a visual image for inspection. For an inspection of the component from multiple angles thereof, the component may be rotated about a rotational axis that usually needs to remain aligned with the x-ray beam. The position of the component relative to the x-ray tube is important to obtain a desired image of the component for an area of interest.

In order to get the desired image or images for the area of interest, it can often be difficult and time consuming to get the desired area of interest aligned with the rotational axis aligned with the x-ray tube, particularly when the component, or the area of interest of the component, is small. Fine adjustments of the position of the area of interest of the component relative to the axis of rotation aligned with the x-ray tube are often needed in order to obtain the desired image. Currently, these fine adjustments of the component's position are accomplished by hand. That is, the operator may roughly position the component with mechanical assistance, but then moves the component by hand for fine-tuning into the correct position for obtaining the desired image scan. The correct position is, thus, often determined by using trial and error and often requires multiple, time-consuming adjustments. Because this is not precise and the operator does not know exactly the coordinates of the position of the component after several of these fine adjustments, it is not easily repeatable. Also, to protect the operator from overexposure to radiation, the operator cannot adjust the component by hand when the x-ray tube is providing an x-ray beam. Thus, the operator typically has to position the item in one position, close a door to the system after withdrawing from the inspection area, turn on the x-ray tube, and review a test image of the component to check alignment. If the alignment is not correct, the operator then has to turn off the x-ray tube, open the door and enter the area to re-position the item into another position that may provide a better image. This positioning process is repeated until the alignment is correct and the desired image is obtained. This back-and-forth adjustment process can be quite time consuming and inefficient.

In view of the foregoing, there is a need in the art for a more efficient manner for fine adjustment of the position of the component relative to the x-ray tube.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one embodiment, relates to a component imaging system. The system may include a frame, wherein a x-ray detector is mountable at a first end of the frame and a x-ray tube is mountable at a second end of the frame opposite the first end. The system may also include a rotatable platform positioned between a first end of the frame and the second end of the frame, the rotatable platform being rotatable about a first rotational axis. The system may still further include a turntable having: a stage platform for holding a component having an area of interest, the area of interest having a rotational axis; and a mounting plate for engagement with the rotatable platform, the mounting plate rotating with the rotatable platform about the first rotational axis. The stage platform may be moveable in a first direction from a starting position to an imaging position, where the first direction is perpendicular to the first rotational axis. In some embodiments, the system may be configured such that in the imaging position, the rotational axis of the area of interest is aligned with the first rotational axis. In some embodiments, the system may further include a controller for controlling movement of the stage platform from the starting position to the imaging position.

In still additional embodiments, the system may include a first rail assembly connected to the stage platform, the first rail assembly having a rail, a guide slidably connected to the rail, and a motor for actuating movement of the guide relative to the rail. A first set of contacts may be provided on the mounting plate of the turntable, with the first set of contacts in electrical communication with the motor of the first rail assembly. Electrical leads for electrical communication with the controller may also be provided, with the electrical leads fixedly positioned relative to the rotatable platform. When the first set of contacts are in electrical communication with the electrical leads, an electrical signal can be provided to the motor to actuate movement of the guide relative to the rail to move the stage platform in the first direction. Moreover, in further embodiments, the system may include a second rail assembly connected to the first rail assembly, the second rail assembly also having a rail, a guide slidably connected to the rail, and a motor for actuating movement of the guide relative to the rail. The second rail assembly may be connected to the first rail assembly such that the rail of the second rail assembly is perpendicular the rail of the first rail assembly. A second set of contacts may be provided on the mounting plate of the turntable, with the second set of contacts in electrical communication with the motor of the second rail assembly. In some embodiments, the second set of contacts may be positioned on the mounting table about 90 degrees apart from the first set of contacts. Like with the first rail assembly, when the second set of contacts are in electrical communication with the electrical leads, an electrical signal can be provided to the motor of the second rail assembly to actuate movement of the guide of the second rail assembly relative to the rail of the second rail assembly to move the stage platform in a linear direction that is nonparallel, and in some embodiments perpendicular, with the first direction.

In still further embodiments, the system may additionally include a platform track assembly, wherein the rotatable platform is mounted to the track assembly for linear movement of the rotatable platform. A base track assembly may extend between the first end and the second end of the frame. The platform track assembly may be connected to the base track assembly for linear movement of the rotatable platform relative to the first end and the second end of the frame.

The present disclosure, in another embodiment, relates to a manipulator for a component imaging system. The manipulator may include a mounting plate rotatable about a first rotational axis from a first position to a second position, and a stage platform having a surface for holding a component having an area of interest to be imaged, the stage platform having a center and a central axis perpendicular to the surface and running through the center. The stage platform may be rotatable about the first rotational axis with the mounting plate, and the stage platform may be moveable radially relative to the mounting plate from an initial position to an imaging position, wherein in the imaging position the central axis is unaligned with the first rotational axis. A first rail assembly for radially moving the stage platform and a controller configured for selectable electrical communication with the first rail assembly, may each be provided. When the controller is in electrical communication with the first rail assembly, the controller may send a signal to a motor of the first rail assembly to move the stage platform along the rail assembly. In some embodiments, the manipulator may include two sets of contacts, and the controller may be configured for selectable electrical communication between the two sets of contacts. In yet further embodiments, a second rail assembly for radially moving the stage platform in a direction different than provided by the first rail assembly may be provided. The first rail assembly may be in electrical communication with a first set of the two sets of contacts and the second rail assembly may be in electrical communication with a second set of the two sets of contacts.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying figures, in which:

DETAILED DESCRIPTION

Figure 1:
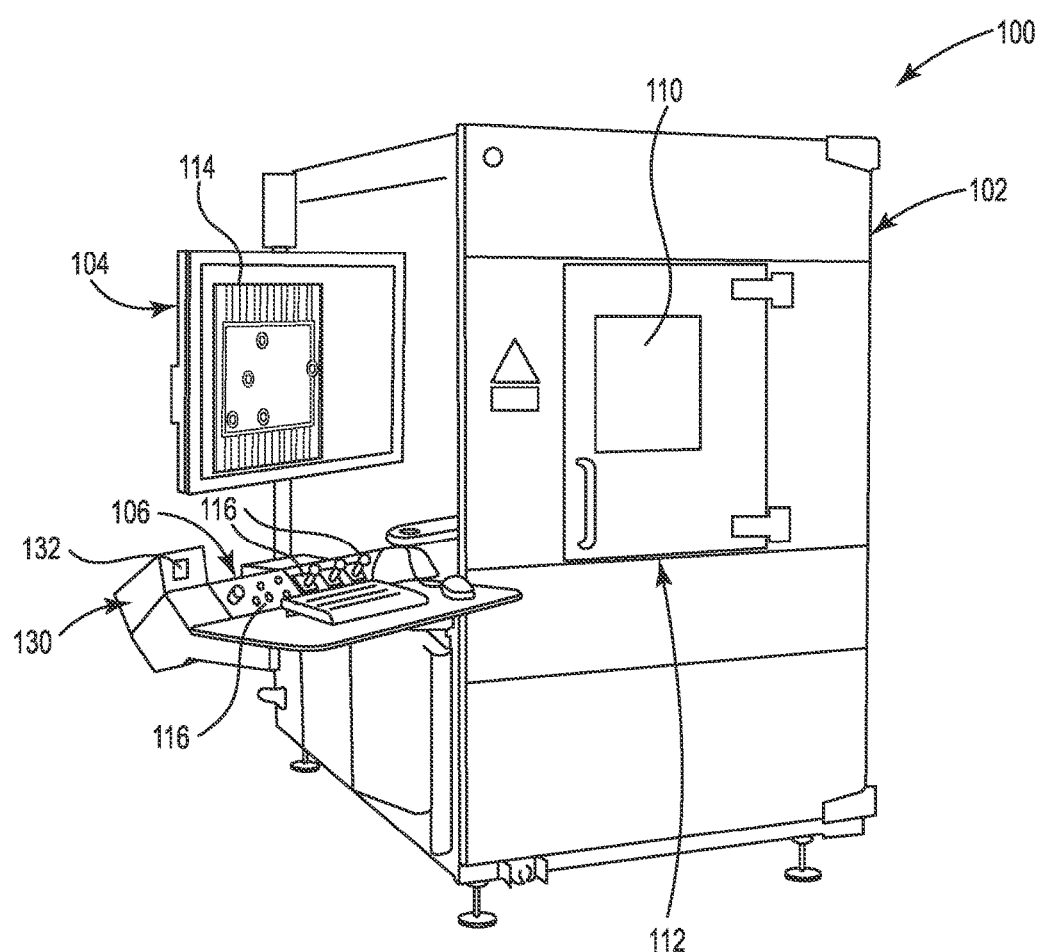
FIG. 1 is a perspective view of one embodiment of a component imaging system of the present disclosure.

The present disclosure relates to novel and advantageous systems and methods for imaging components using x-ray computed tomography (CT) scan technology. More particularly, the present disclosure relates to a turntable for more efficient and accurate positioning of a component to be imaged relative to an x-ray tube.

FIGS. 1-5 show embodiments of a component imaging system of the present disclosure. FIGS. 1-5 each show a cabinet-style imaging system, although embodiments of the turntables as described herein may also be suited for large envelope systems, such as those described further below with respect to FIGS. 11-12. According to one embodiment shown in FIG. 1, the component imaging system 100 comprises a cabinet 102, a display screen 104, and a control panel 106. The cabinet 102 comprises an inspection area 110, which contains an x-ray tube, and a door 112 for sealing off the inspection area 110 when the x-ray tube is turned on and emitting x-rays. A component is positioned within the inspection area 110 for imaging. Among other things, the display screen 104 displays an image of the component 114 when the x-ray tube is on. The control panel 106 may include multiple controllers 116 for controlling at least the x-ray tube and certain positioning devices of the component imaging system described herein.

Figure 2:
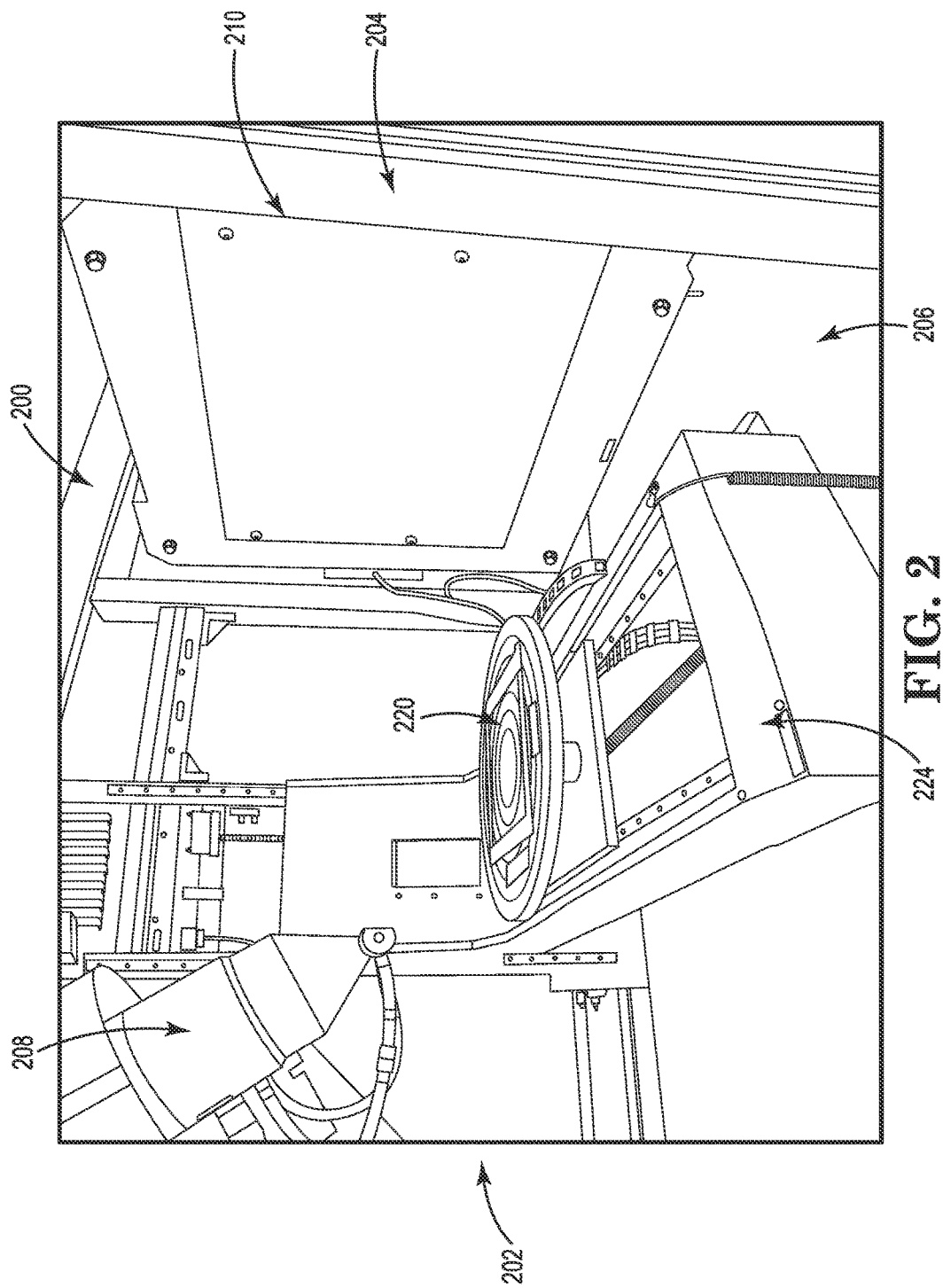
FIG. 2 is a perspective view from the interior of one embodiment of a component imaging system such as the one shown in FIG. 1.

FIG. 2 shows a view of the inspection area of a component imaging system 200. As shown in FIG. 2, component imaging system 200 may comprise a first end (shown generally at 202), a second end (shown generally at 204), and a base 206 therebetween. In some embodiments, the base 206 may comprise a solid floor or it may comprise rails that connect the first end 202 to the second end 204 in a longitudinal direction. In at least one embodiment, at least one x-ray tube 208 may be mounted at the first end, and an x-ray detector 210 may be mounted at the second end opposite the x-ray tube 208. The x-ray tube 208 may be any suitable x-ray tube for emitting the desired x-ray beam for analysis and inspection of components. The x-ray detector 210 may be any detector compatible with x-ray tube 208. In some embodiments, multiple x-ray tubes may be utilized. In some embodiments with multiple x-ray tubes, the x-ray tubes may be mounted to allow repositioning of at least one of the x-ray tubes as discussed in co-owned and co-pending application U.S. Ser. No. 15/220,851, entitled "Shifting Mechanism for Dual X-Ray Tube Imaging System," filed on Jul. 27, 2016, which is hereby incorporated herein by reference in its entirety. A rotatable platform 220 may be positioned on, or otherwise connected to, the base 206 along a platform track assembly 224. The rotatable foundation platform 220 may be moved linearly along the track assembly 224 in a direction generally perpendicular to the longitudinal direction of the base 206 or otherwise generally across the x-ray field emitted by the x-ray tube 208. The rotatable platform 220 is rotatable about a rotational axis thereof. A component may be positioned within the inspection area of the component imaging system 200 on top of the rotatable platform 220. In some uses, the component may be rotated while the x-ray tube is turned on to obtain and display, for example on display screen 104, a set of images of different sides or perspectives of the component. In order to display consistently aligned images of an area of interest of the component at different perspectives as it is rotated, the rotational axis of the area of interest of the component may desirably or even preferably be aligned with the rotational axis of the rotatable platform. Consequently, the position of the component relative to the rotatable platform 220 can be important to obtaining the desired set of images. Referring again to FIG. 1, if the image displayed on the display screen is not properly centered on the desired area of interest of the component, in conventional systems, the operator needs to turn off the x-ray tube 208, open the door 112, adjust the position of the component on the rotatable platform 220, close the door 112, turn on the x-ray tube 208, and review a new image displayed on the display screen to determine whether the desired area of interest is now properly centered. Any adjustments of the position of the component are currently completed by hand using trial and error, and typically comprises several iterations of the foregoing described process, which can be both frustrating and time consuming.

Figure 3:
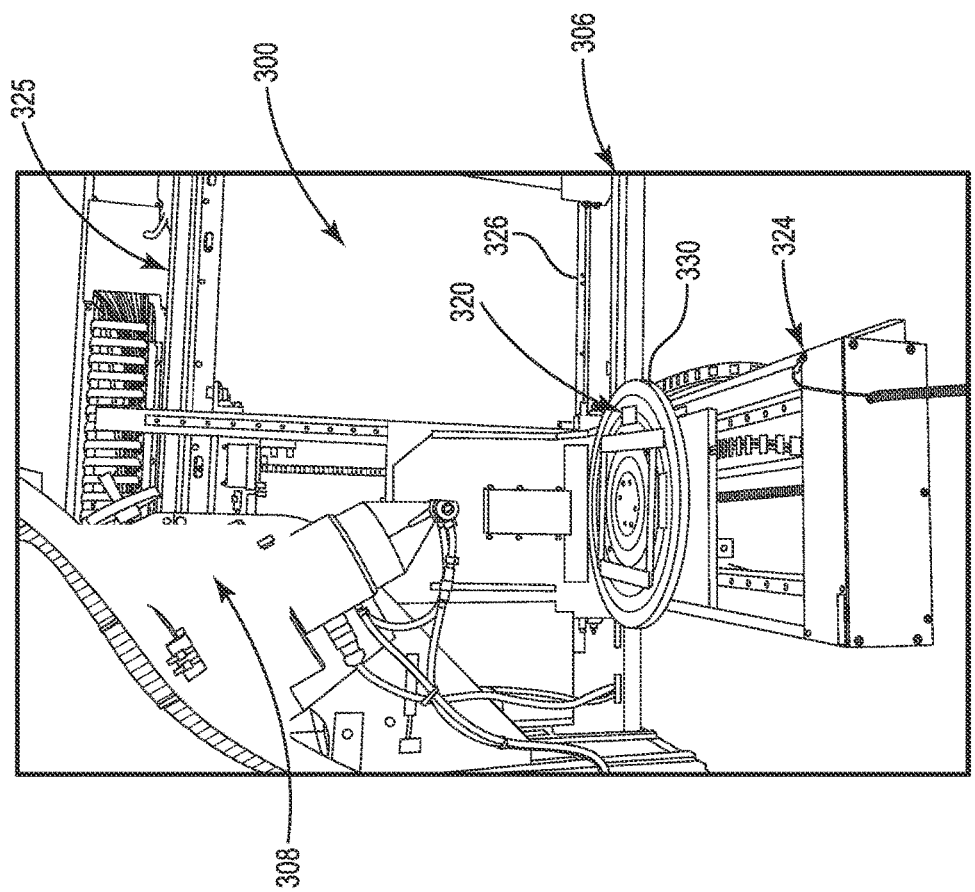
FIG. 3 is a side view of one embodiment of a component imaging system of the present disclosure.
Figure 4:
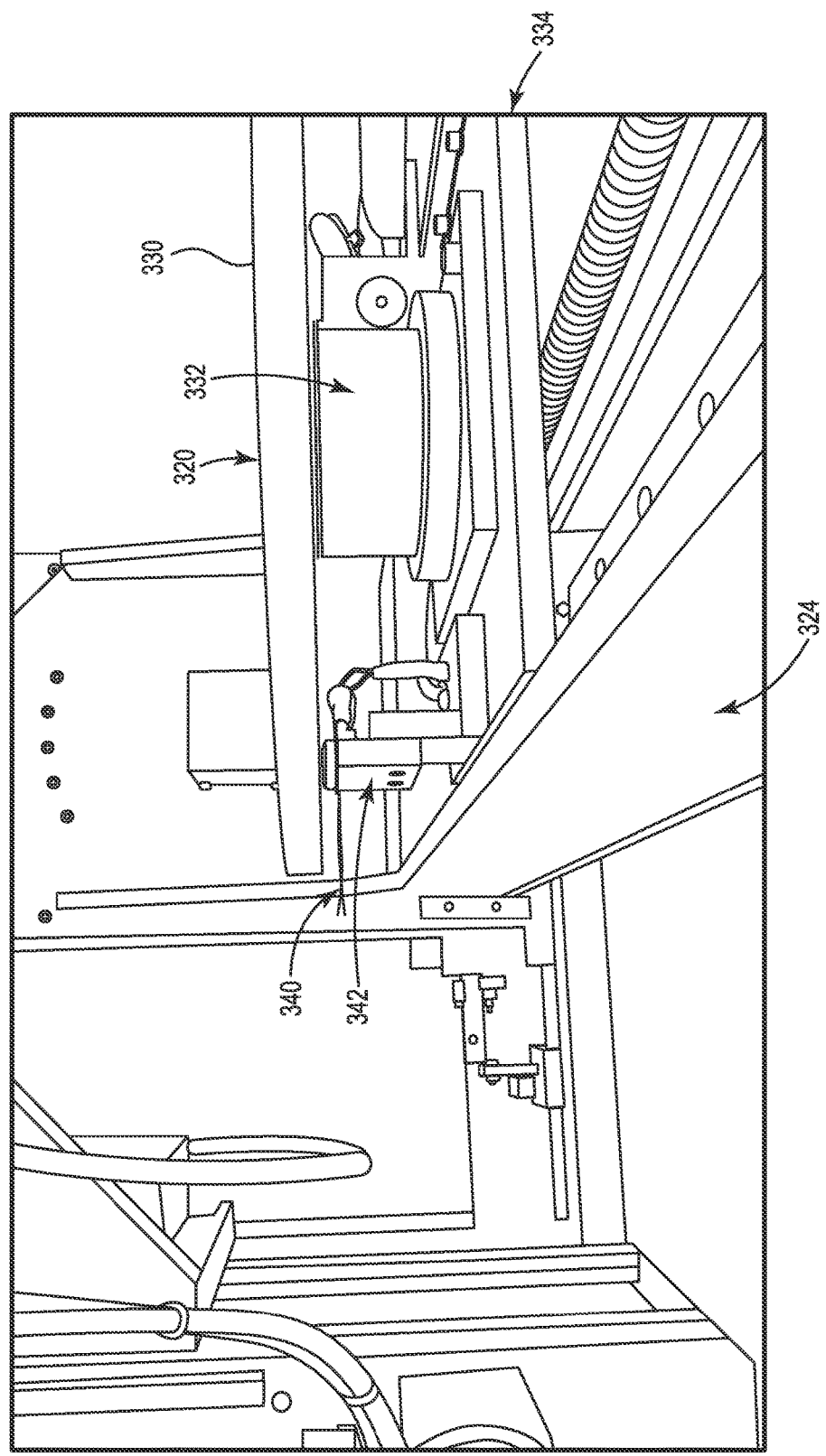
FIG. 4 is a side view of the base platform of the component imaging system shown in FIG. 3.
Figure 5:
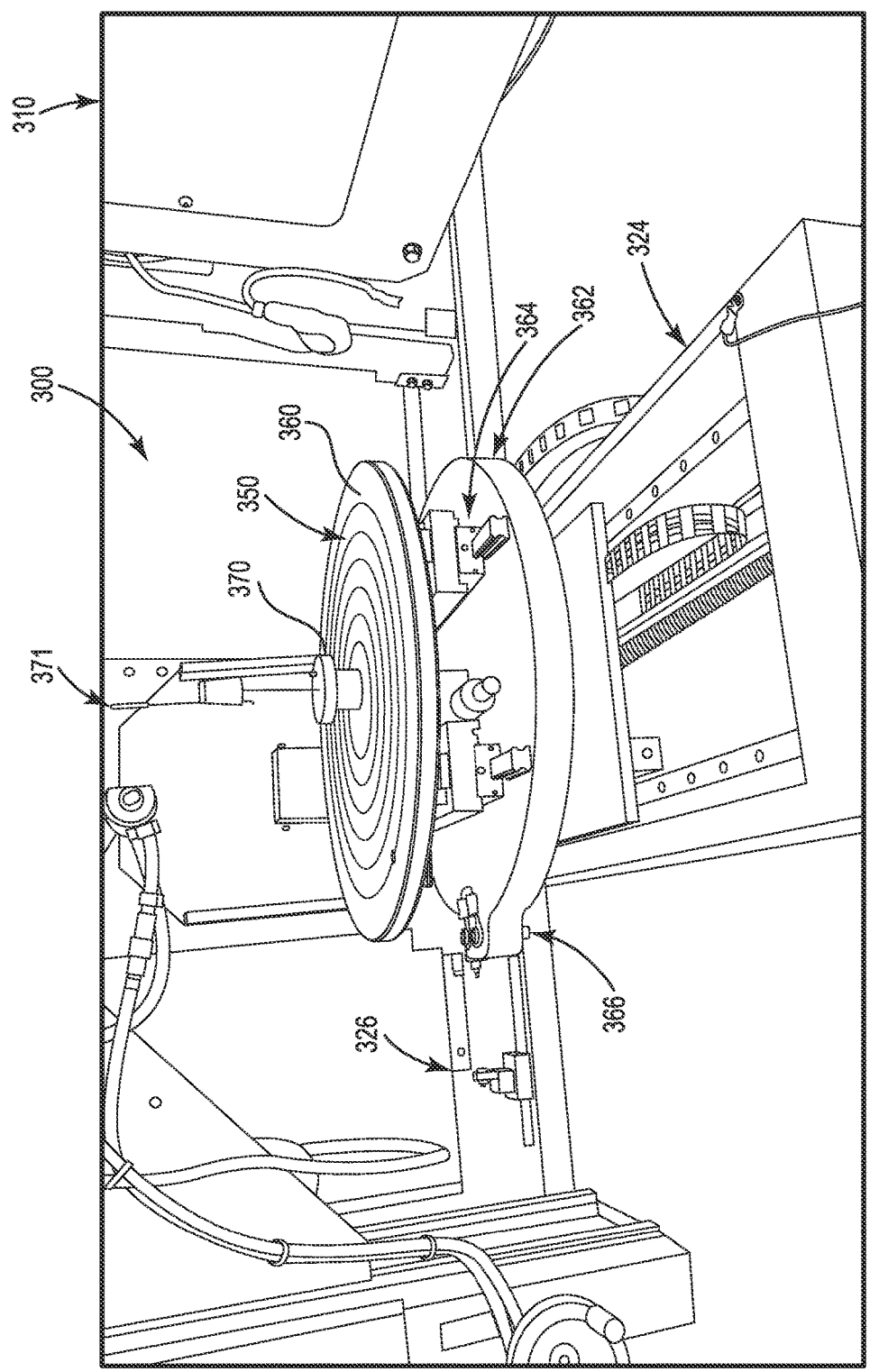
FIG. 5 is a side view of the component imaging system shown in FIG. 3 with a stage platform of the present disclosure mounted on top of the base platform.

FIGS. 3-5 show various side views of one embodiment of the inspection area of a component imaging system 300. The component imaging system as shown comprises at least an x-ray tube 308, a base track assembly 306, a platform track assembly 324 connected to the base track assembly 306 and extending in a direction perpendicular to the direction of the base track assembly 306, and a rotatable platform 320 positioned on, or otherwise connected to, the platform track assembly 324. As described above, the rotatable platform 320 is rotatable about a rotational axis thereof, and the rotatable platform 320 may be moveably mounted to the platform track assembly 324 and may move linearly along the platform track assembly 324 in a direction perpendicular to the base track assembly 306. Thus, the rotatable platform 320 may be linearly moved in the direction perpendicular to the base track assembly 306 as well as be rotated about a rotational axis of the rotatable platform 320. The rotatable platform 320 may comprise a top plate 330 rotatably mounted to a bushing 332, which is mounted to a track plate 334 engaged with the platform track assembly 324, as shown in FIG. 4. The platform track assembly 324 is also movable along the base track assembly 306 toward or away from the x-ray tube 308. The base track assembly 306 may typically include at least one of a top track 325 and a bottom track 326 for actuating and/or guiding linear movement of the platform track assembly 324 therealong. In other embodiments, any other conventional assembly for moving the platform track assembly toward or away from the x-ray tube 308 can be used. In general, the platform track assembly 324 may be moved linearly along at least one of the tracks 325, 326 of the base track assembly 306, or other like assembly, so as to correspondingly position the rotatable platform 320 nearer to or further from the x-ray tube 308, as desired. In some embodiments, the x-ray tube 308 may similarly have an x-ray track assembly that allows the x-ray tube to move linearly in a vertical direction relative the rotatable platform 320. Although the rotatable platform 320 may be linearly moved along the platform track assembly 324 and linearly moved toward the x-ray tube 308 or away from the x-ray tube 308, as just described, this relative movement does not provide the desired or required fine adjustment of the position of the component on the rotatable platform 320 relative to the rotational axis of the rotatable platform. As indicated above, the position of the component often needs to be further adjusted on the rotatable platform 320 in order to align a rotational axis of the desired area of interest of the component with the rotational axis of the rotatable platform for consistent rotational imaging of the component. Such adjustments are currently completed by hand, and as previously discussed, involve turning off the x-ray tube, opening the cabinet door, adjusting the position of the component essentially by guesswork, closing the cabinet door, turning on the x-ray tube, and examining the new image to see whether the component is now in the desired alignment. Consequently, it is desirable to have remote, mechanical or electromechanical adjustment of the position of the component while the x-ray tube is turned on to allow an operator to view the image while adjusting the position of the component, in order to reduce the time and inefficiency of the alignment process.

Figure 6:
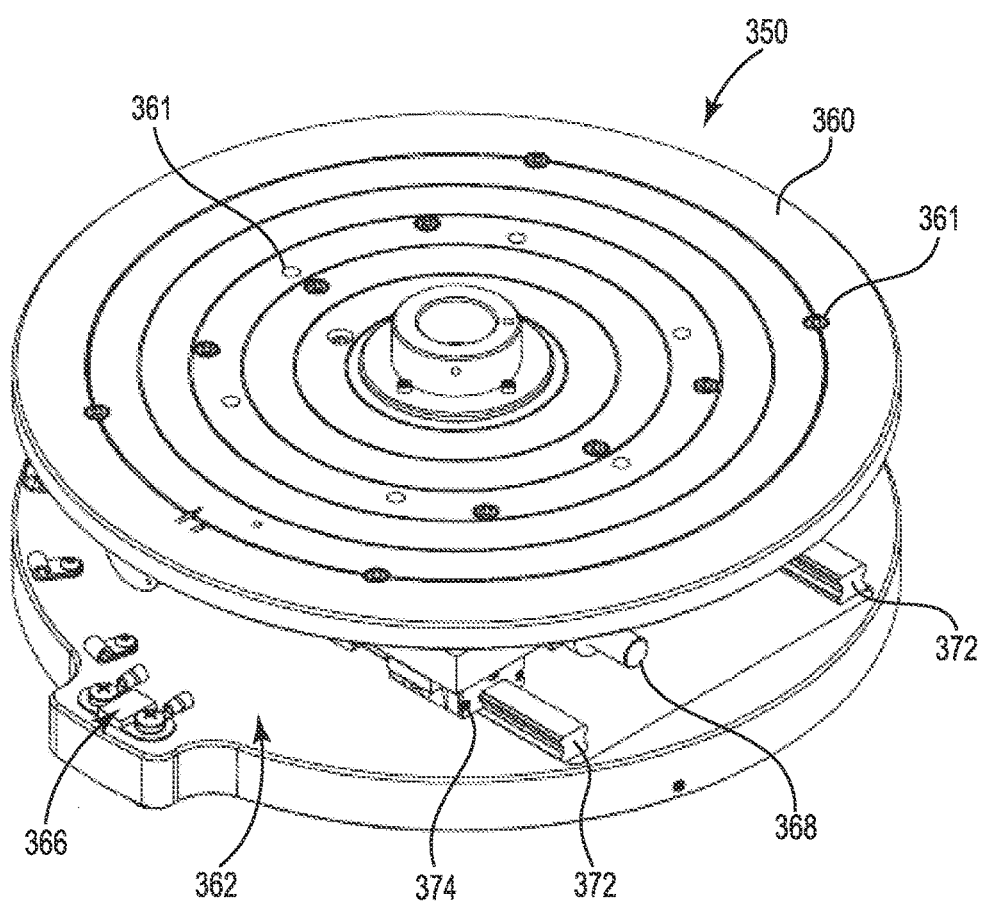
FIG. 6 is a perspective view of one embodiment of the turntable of the present disclosure.
Figure 7:
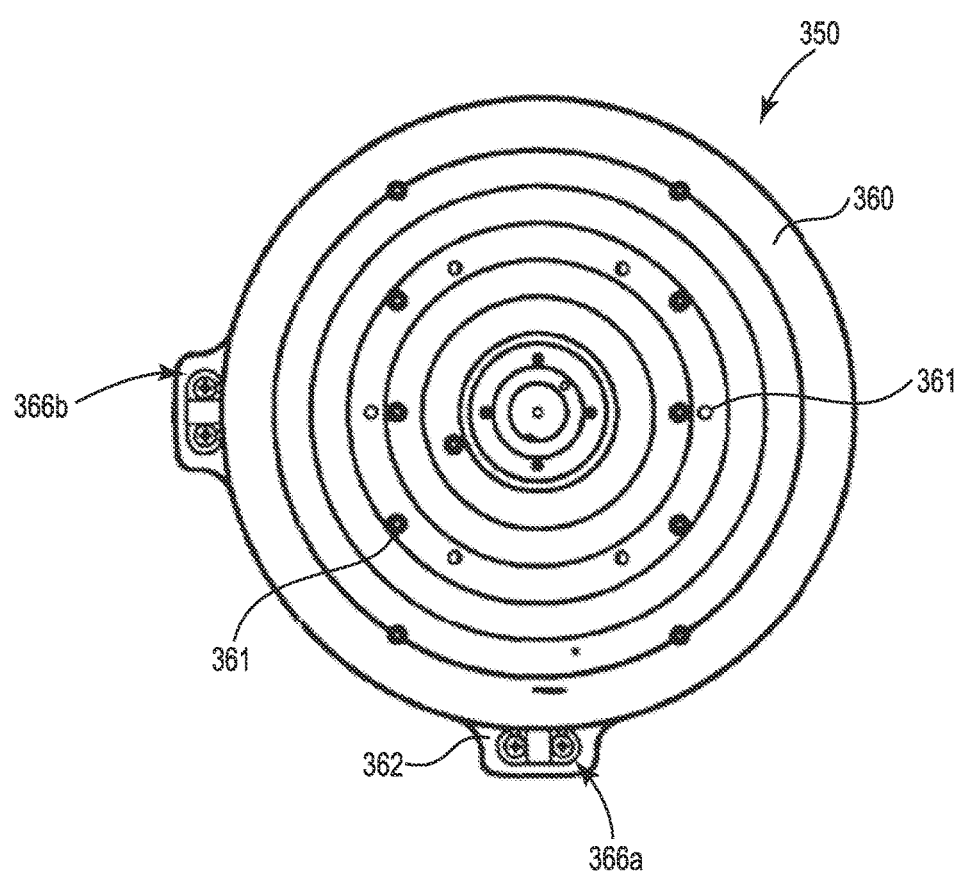
FIG. 7 is a top view of the turntable shown in FIG. 6.
Figure 8:
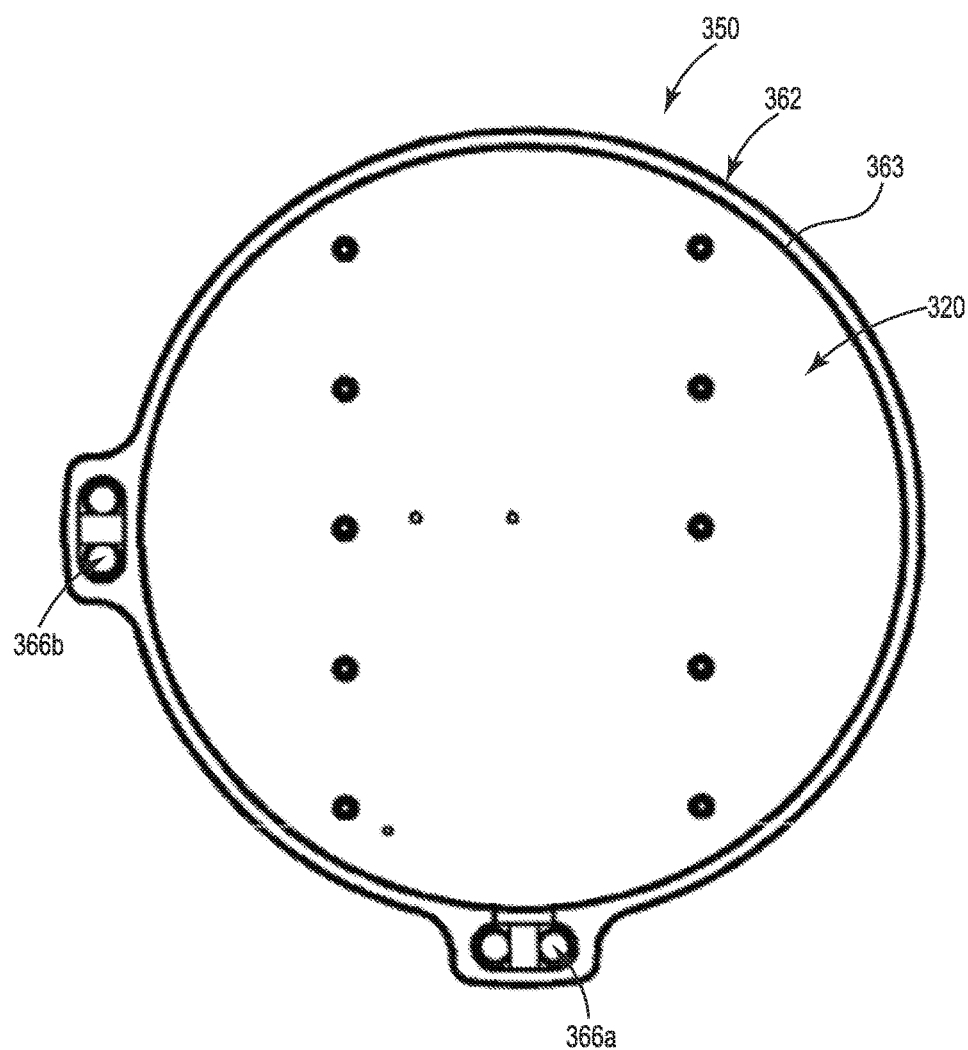
FIG. 8 is a bottom view of the turntable shown in FIGS. 6-7.

Thus, in one embodiment, the component imaging system may further include a turntable mounted onto or otherwise operably coupled with the rotatable platform 320 and rotatable therewith. In at least one embodiment, the rotatable platform 320, the platform track assembly 324, and the turntable may define a manipulator. FIG. 5 shows a side view of the component imaging system 300 with a turntable 350 of the present disclosure mounted onto the rotatable platform 320, and FIGS. 6-8 show perspective, top, and bottom views of one embodiment of the turntable 350. In one embodiment, the turntable 350 may comprise a stage platform 360, a mounting plate 362, and at least one rail assembly 364 positioned between the stage platform 360 and the mounting plate 362 for linear or radial movement of the stage platform 360 relative to the mounting plate 362. In one embodiment, the turntable 350 may have two rail assemblies 364 for linear or radial movement of the stage platform 360 in multiple directions, for example two directions, relative to the mounting plate 362. In a further embodiment, two directions of movement may be generally perpendicular to each other. In other embodiments, even more than two rail assemblies may be used or combinations of one or more other mechanical or electromechanical assemblies, such as but not limited to bearing assemblies, may be provided that each permit movement of the stage platform 360 in one or more directions. In at least one embodiment, the component may be rested on, mounted onto, secured to, or held on the stage platform 360. In some embodiments, the stage platform 360 may comprise one or more mounting holes 361 for mounting fixtures configured for holding or securing a component on the stage platform. FIG. 5 shows a component 371 mounted onto the stage platform 360 via a mount 370 secured to the stage platform. The stage platform 360 may be a plate similar to the top plate 330 of the rotatable platform 320, which may be a plate such as those conventionally used for the manipulators of CT imaging systems. The stage platform 360 may be round, rectangular, or may have other configurations suitable for mounting components of various sizes and shapes. The mounting plate 362 likewise may be round, rectangular, or may have other configurations suitable for mounting the turntable 350 to the rotatable foundation platform 320. In at least one embodiment, the mounting plate 362 may be configured with a recess 363 as shown in FIG. 8 to receive, and in some cases snuggly receive, the top plate 330 of the rotatable platform 320, thereby securing the mounting plate 362 to the rotatable platform 320 so that the turntable 350 rotates with the rotatable platform 320 and moves linearly with the rotatable platform 320 along platform track assembly 324. The recess 363 in one embodiment may be sized, shaped, and configured similar to the shape and size of the top plate 330 so as to permit the mounting plate 362 to mount or secure to the top plate 330, even without further attachment means. However, in other embodiments, the mounting plate 362 may mount onto or secure to the top plate 330 for rotational and linear movement therewith using any conventional attachment means or devices, whether or not a recess 363 for receiving the top plate 330 is provided. In at least one embodiment, the mounting plate may be concentric with the plate 330 of the rotatable platform 320. In at least one embodiment, the mounting plate 362 may be coaxial with the rotational axis of the rotatable platform 320. In one embodiment, each rail assembly 364 may comprise at least a motor 368, at least one rail 372 and at least one guide 374 for each rail, each guide 374 slidably engaged with the rail 372 and actuated by the motor 368. Where at least two rail assemblies 364 are provided, the rails 372 of one rail assembly 364, according to one embodiment of the present disclosure, may be positioned generally perpendicular to the rails 372 of the other rail assembly 364. By positioning the two rail assemblies perpendicular to one another, the position of the stage platform 360 (and thus, the position of a component rested or mounted thereon) can be suitably adjusted relative the mounting plate 362 and thus top plate 330 into any suitable position (within the boundaries permitted by the rail systems) in an x-y plane parallel with the mounting plate 362 and thus top plate 360.

As shown best in FIG. 4, the rotatable platform 320 may have a set of electrical leads 340. The electrical leads 340 may be mounted to a lead mounting bracket 342, which may be attached to the track plate 334 so that the electrical leads 340 move linearly with the rotatable platform 320 along platform track assembly 324 but do not rotate with the rotatable platform 320. The electrical leads 340 may be in electrical communication with a controller. The controller may be a controller 116 on the control panel 106, or the controller may be a separate controller 130, as shown in FIG. 1. The controller 130 may comprise at least one toggle switch, dial, joystick, or other input device 132 for controlling movement of the stage platform. As shown in at least FIGS. 5-8, the mounting plate 362 may further comprise at least one set of contacts 366 for electrical engagement with the electrical leads 340. The set of contacts 366 may comprise two or more contacts. Each set of contacts 366 may be exposed from the bottom of the mounting plate 362 and configured or aligned about the mounting plate so as to electrically couple with the electrical leads 340 when positioned over the electrical leads, as will be further explained below. In some embodiments, each set of contacts 366 may comprise as many contacts as the number of leads in the set of electrical leads 340. Each set of contacts 366 may be in electrical communication with a motor 368 associated with a corresponding rail assembly 364. When the set of contacts 366 are engaged with the electrical leads, the motor 368 may be actuated to move the stage platform 360 in a direction, based on signals received from the controller 130, along the corresponding rail assembly 364. In at least one embodiment, one set of contacts 366 is provided for each rail assembly. In embodiments with at least two rail assemblies 364, the mounting plate 362 may comprise at least two sets of contacts 366a, 366b, as shown at least in FIGS. 7-8. In at least one embodiment, the sets of contacts 366a, 366b are positioned at the same angles relative to one another as the respective rail assemblies 364 are positioned relative to one another. In one embodiment, a first set of contacts 366a is positioned on the mounting plate at about 90 degrees apart, relative a central axis of the mounting plate, from a second set of contacts 366b. By positioning the contacts about 90 degrees apart from one another in this manner, an operator can easily switch from one set of contacts being electrically connected with the leads 340 to the other being electrically connected with the leads 340, and accordingly, the position of the stage platform 360 (and thus, the position of a component rested or mounted thereon) can be efficiently adjusted into position in the above-mentioned x-y plane with movements along two (or more in some embodiments) simple axes. Of course, any other suitable number of directional movements may be used, and other relative positions of the sets of contacts, as well as additional sets of contacts, are contemplated by this disclosure.

In one embodiment, when one set of contacts 366 is in electrical engagement with the electrical leads 340 and controlled by electrical signals received from the controller 130, the motor 368 may actuate movement of the stage platform 360 in a first direction along the rails of the corresponding rail assembly. Rotation of the mounting plate 362, by rotation of the rotatable platform 320, may disengage the connection between the first set of contacts and the electrical leads 340. In one embodiment, a 90-degree rotation of the mounting plate 362 in a first rotational direction, by rotation of the rotatable platform 320, may engage the second set of contacts with the electrical leads 340. When the second set of contacts is in electrical engagement with the electrical leads and controlled by electrical signals received from the controller 130, the stage platform 360 can be moved in a second direction perpendicular to the first direction relative the mounting plate 362 via the motor and corresponding rail assembly electrically connected with the second set of contacts. Thus, the position of the stage platform 360 relative to the rotatable foundation platform 320 (and therefore, its rotational axis) may be known or identified and controlled by an operator, even while the x-ray tube is turned on.

Figure 9:
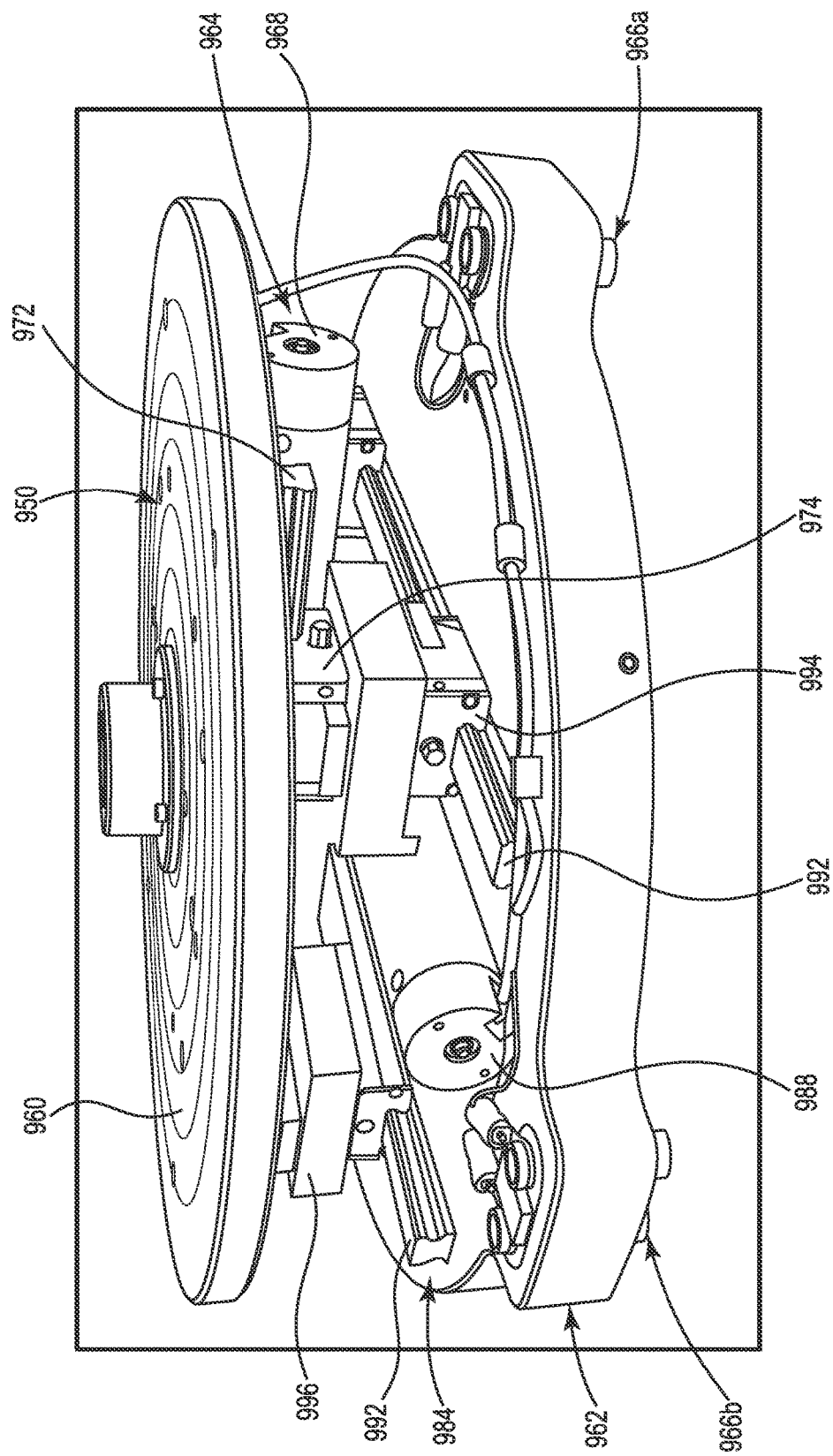
FIG. 9 is a side view of one embodiment of the turntable of the present disclosure.
Figure 10:
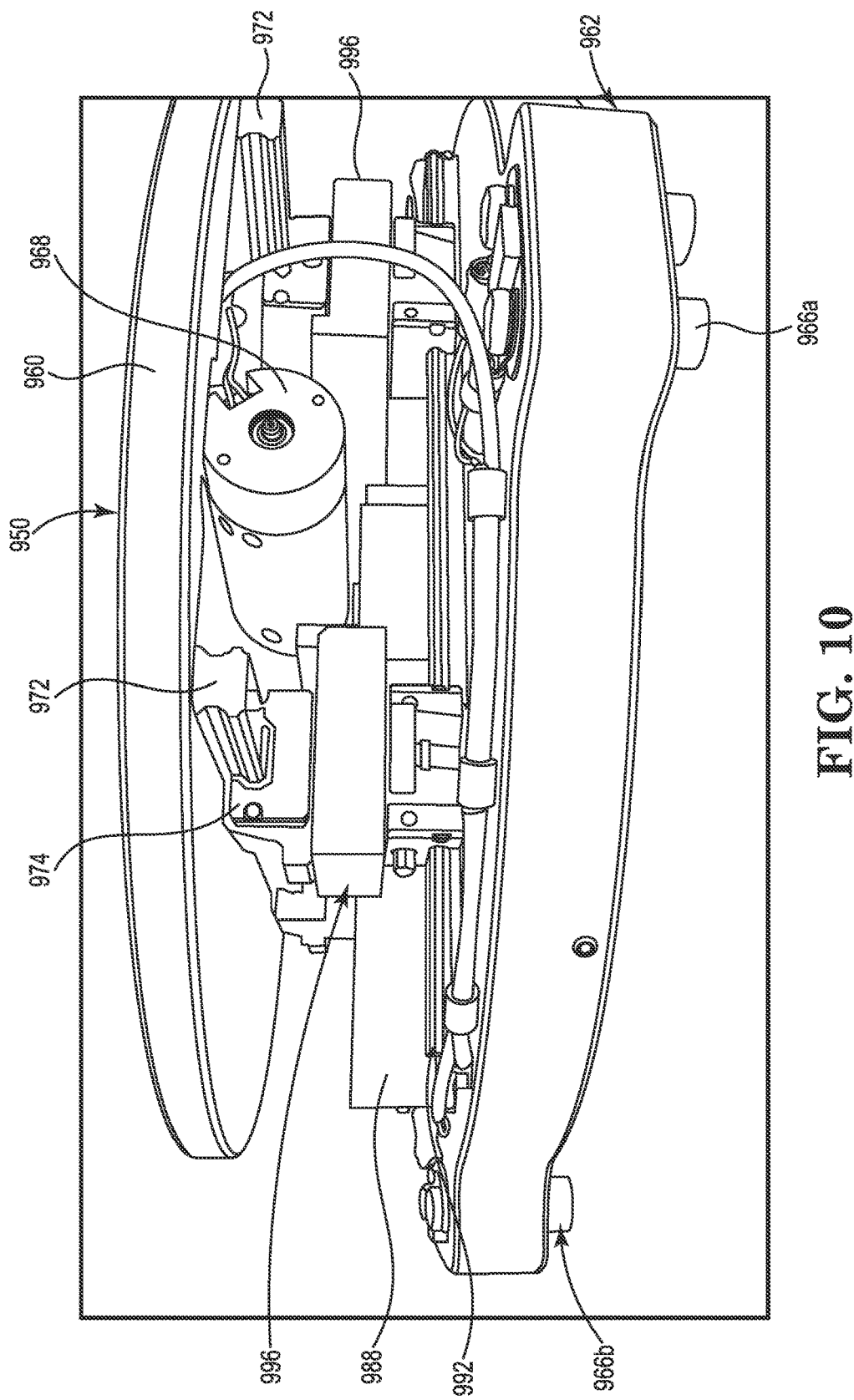
FIG. 10 is a side view of the stage platform shown in FIG. 9.

FIGS. 9-10 show one embodiment of a turntable 950 that is not yet engaged with a rotatable platform of a component imaging system. As shown, the turntable 950 comprises a first stage platform 960, a mounting plate 962, a first rail assembly 964 positioned between the first stage platform 960 and the mounting plate 962 for linear or radial movement of the first stage platform 960 relative to the mounting plate 962, and a second rail assembly 984 positioned between the first rail assembly 964 and the mounting plate 962 also for linear or radial movement of the first stage platform 960 relative to the mounting plate 962, but in a different linear or radial direction than provided by the first rail assembly 964. In this embodiment, the mounting plate 962 comprises a first set of contacts 966a positioned about 90 degrees apart from a second set of contacts 966b. Each rail assembly 964, 984 comprises at least a motor 968, 988; a pair of rails 972, 992; and at least one guide 974, 994 for each rail. Each guide 974, 994 is slidably engaged with the respective rail 972, 992 and relative movement between the guide 974, 994 and its respective rail 972, 992 is actuated by a drive mechanism of the respective motor 968, 988. As shown, the first pair of rails 992 may be positioned generally perpendicular to the second set of rails 992. As also shown, spacers 996 may be used to separate the rail assemblies 964, 984. The first motor 968 may also be positioned generally perpendicular to the second motor 988 and may be positioned between rails 972. The second motor 988 may likewise be positioned between rails 992. As shown, rails 972 may be mounted to a bottom surface of the first stage platform 960 and rails 992 may be mounted to a top surface of the mounting platform 962. Although the disclosure herein describes using linear rail systems to move the stage platform 960 in linear directions, the system could use ball screws or other linear movement devices to move the stage platform 960 to position the component in a desired location, as described herein. Additionally or alternatively, the system could use magnets, other magnetic devices, and/or electromechanical devices other than those described in detail herein to move the stage platform 960 to position the component, as described herein, using linear or non-linear movement or a combination thereof.

In embodiments of the disclosure, a display screen 104, as shown in FIG. 1, may be visible to an operator, wherein the display screen may display a real-time or substantially real-time x-ray image of the component. In some embodiments, the display screen may display the current position of the component relative to the rotational axis of the foundation platform and/or the x-ray beam. The operator may make adjustments to the current position of the component based on the information displayed on the display screen regarding the component's position relative to the rotational axis of the foundation platform and/or the x-ray beam. In typical embodiments, this adjustment or motion of the component will be in a plane parallel to the x-ray detector. In some embodiments, a component may be mounted to the stage platform while the stage platform is in a starting neutral position. In the starting or neutral position, the stage platform may be coaxial with the mounting plate, which may be coaxial with the rotatable platform. However, other alignments could be used as the starting or neutral position. In at least one embodiment, the mounting plate is generally constantly coaxial with the rotatable platform. By way of a controller, the operator can rotate the rotatable platform, which rotates the mounting plate of the turntable, until a first set of contacts on the mounting plate engages with electrical leads extending outwardly from the rotatable foundation platform. Once engaged, the operator can selectively actuate a first motor corresponding to, and electrically coupled with, the first set of contacts using the controller in order to move the stage platform forward or backward in a first linear direction along the rails of a first rail assembly corresponding to the first motor, from an initial or starting position to an adjusted position. In at least one embodiment, the distance the stage platform is moved forward or backward may be known or recorded. In the adjusted position, the stage platform need not, and in many cases won't, be coaxial with the mounting plate, but it remains rotatable about the rotational axis of the rotatable foundation platform. This first adjusted position may still not be the final position for obtaining the desired image, depending on the alignment of the desired area of the component as shown on the display screen. In at least one embodiment, by way of input on the controller, the operator can rotate, in some cases incrementally, the mounting plate in a rotational direction a defined amount of degrees (in one embodiment, about 90 degrees) until a second set of contacts on the mounting plate engages with the electrical leads. Once engaged, the operator can selectively actuate a second motor corresponding to, and electrically coupled with, the second set of contacts using the controller to move the stage platform forward or backward in a second linear direction along the rails of a second assembly corresponding to the second motor, to a second adjusted position. Again, in typical embodiments, this adjustment or motion of the component will typically be in a plane parallel to the x-ray detector. In one embodiment, if further adjustment is needed, the operator can continue to rotate the mounting plate further or rotate the mounting plate back until the first set of contacts reengages with the electrical leads. Additionally or alternatively, the operator can continue to rotate the mounting plate so that yet another set of contacts, corresponding to another rail assembly, engages with the electrical leads. If necessary or desired, the process of selectively rotating between contacts and actuating the corresponding rail assemblies may continue until the component is in its desired, final position. In one embodiment, in the final position, coordinates of the component in this position relative to the starting, neutral position may be displayed to the operator, so for example, the operator may repeat these coordinates with a second, similar component without additional experimentation.

Figure 11:
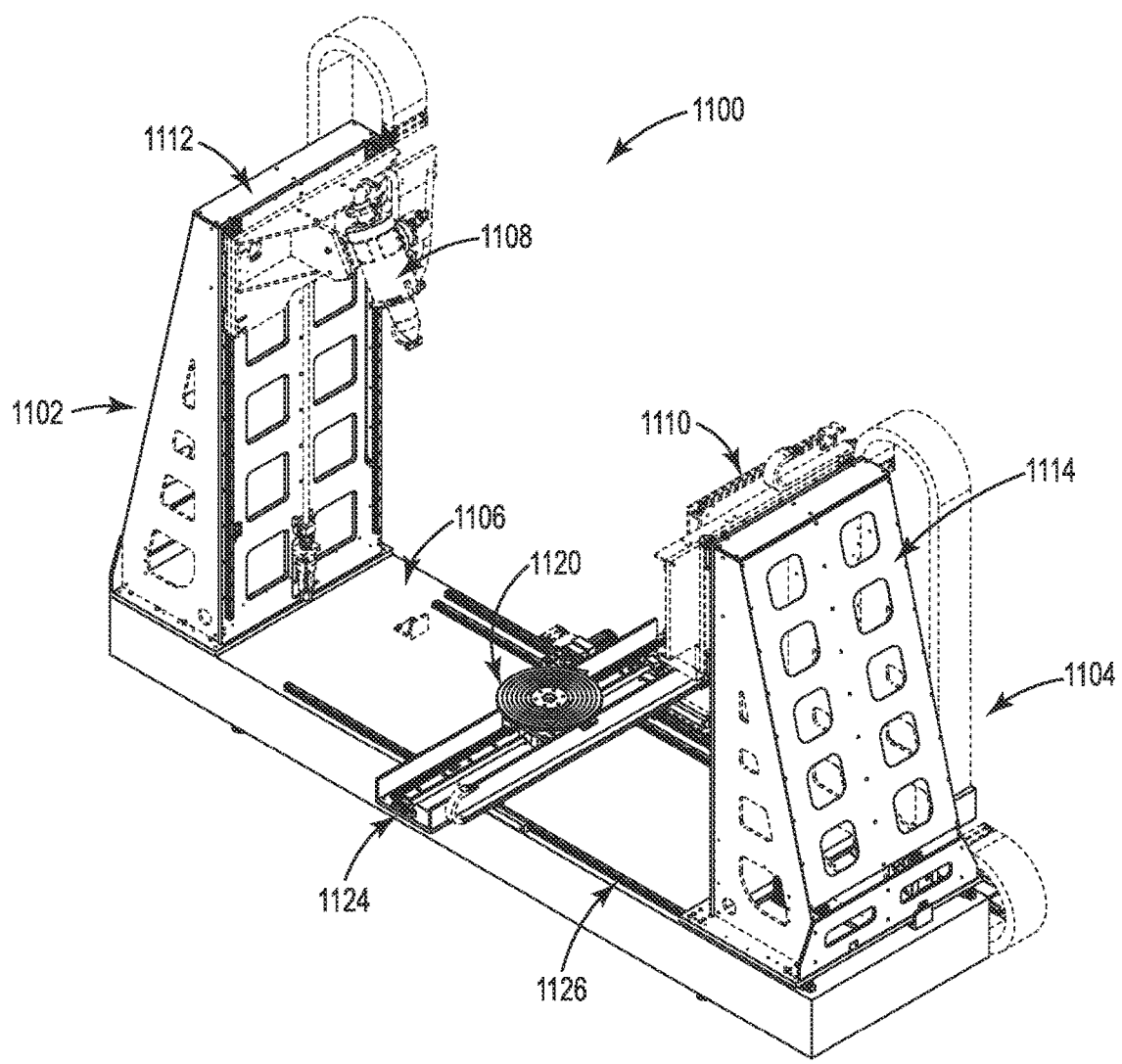
FIG. 11 is an isometric view of one embodiment of a component imaging system of the present disclosure.
Figure 12:
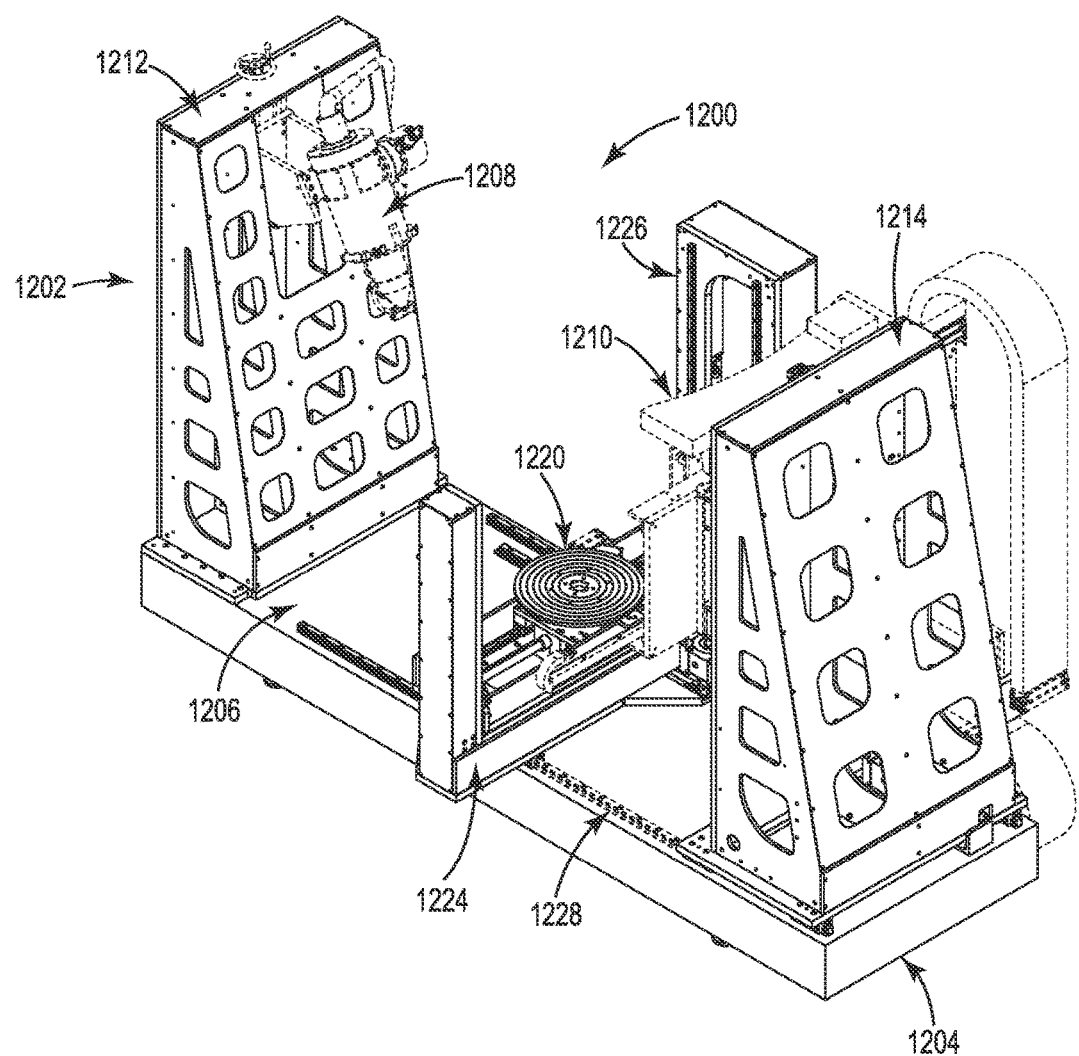
FIG. 12 is an isometric view of one embodiment of a component imaging system of the present disclosure.

While discussed generally with respect to cabinet-style image systems, as indicated above, the various embodiments of the turntables described herein may also be suited for large envelope systems, such as but not limited to those illustrated in FIGS. 11-12. According to one embodiment shown in FIG. 11, component imaging system 1100 may comprise a first end 1102, a second end 1104, and a base 1106 therebetween. In some embodiments, the base 1106 may comprise a solid floor or it may comprise rails that connect the first end 1102 to the second end 1104 in a longitudinal direction. In at least one embodiment, an x-ray tube 1108 may be mounted at the first end 1102, and an x-ray detector 1110 may be mounted at the second end 1104 opposite the x-ray tube 1108. The x-ray tube 1108 may be mounted to a first upright 1112 and the x-ray detector 1110 may be mounted to a second upright 1114. The x-ray tube 1108 may be any suitable x-ray tube for emitting the desired x-ray beam for analysis and inspection of components. The x-ray detector 1110 may be any detector compatible with x-ray tube 1108. In at least one embodiment, the x-ray tube 1108 may be engaged with a track assembly 1116 that allows movement of the x-ray tube 1108 in a vertical direction toward and away from the base 1106. In some embodiments, multiple x-ray tubes 1108 may be mounted onto the first upright 1112. In some embodiments with multiple x-ray tubes, the x-ray tubes may be mounted to allow repositioning of at least one of the x-ray tubes as discussed in co-owned and co-pending U.S. application Ser. No. 15/220,851 which was previously incorporated herein by reference. A rotatable platform 1120 may be positioned on, or otherwise connected to, the base 1106 along a track assembly 1124. The rotatable platform 1120 is rotatable about a central rotational axis thereof. The rotatable foundation platform 1120 may be moved along the track assembly 1124 in direction perpendicular to the longitudinal direction of the base. The track assembly 1124 may be slidably engaged with a track assembly 1126 for moving the rotatable platform 1120 towards and away from the x-ray tube 1108 and/or the x-ray detector 1110. In at least one embodiment, the second upright 1114 may also be slidably engaged with the track assembly 1126 for moving the x-ray detector 1110 towards and away from the x-ray tube 1108, individually or in combination with the rotatable platform 1120. In still other embodiments, the first upright 1112 may also be slidably engaged with a track assembly for movement of the x-ray tube 1108 relative the x-ray detector 1110 and/or rotatable platform 1120. A component for inspection may be positioned on top of the rotatable platform 1120. For the reasons already described above, the component imaging system 1100 may further include a turntable, such as turntable 350, 950 described above, in order to remotely adjust the position of the component relative to the rotational axis of the rotatable platform 1120.

As shown in FIG. 12, another example component imaging system 1200 may comprise a first end 1202, a second end 1204, and a base 1206 therebetween. In at least one embodiment, an x-ray tube 1208 may be mounted at the first end 1202, and an x-ray detector 1210 may be mounted at the second end 1204 opposite the x-ray tube 1208. At least one x-ray tube 1208 may be mounted to a first upright 1212 and at least one x-ray detector 1210 (two are shown in FIG. 12) may be mounted to a second upright 1214. A rotatable foundation platform 1220 may be positioned on, or otherwise connected to, the base 1206 along a track assembly 1224. The rotatable foundation platform 1220 is rotatable about a central rotational axis thereof. The rotatable foundation platform 1220 may be moved along the track assembly 1224 in direction perpendicular to the longitudinal direction of the base. The rotational foundation platform 1220 may also be moved relative to the x-ray tube 1208 and the x-ray detector 1210 in a vertical direction along track assembly 1226, which may be positioned at one end of track assembly 1224. The track assembly 1224 may be slidably engaged with a track assembly 1228 for moving the rotatable platform 1220 towards and away from the x-ray tube 1208 and/or the x-ray detector 1210. In at least one embodiment, the second upright 1214 may also be slidably engaged with the track assembly 1228 for moving the x-ray detector 1210 towards and away from the x-ray tube 1208, individually or in combination with the rotatable platform 1220. In still other embodiments, the first upright 1212 may also be slidably engaged with a track assembly for movement of the x-ray tube 1208 relative the x-ray detector 1210 and/or rotatable platform 1220. Like the system shown in FIG. 11, a turntable such as the ones described above may be mounted onto the rotational foundation platform 1220 for finer adjustments of the position of the component to align a rotational axis of the desired area of interest of the component with the rotational axis of the rotatable foundation platform.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

In the foregoing description, various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

We claim:

1. A component imaging system, the system comprising:
a frame, wherein a x-ray detector is mountable at a first end of the frame and a x-ray tube is mountable at a second end of the frame opposite the first end;
a rotatable platform positioned between a first end of the frame and the second end of the frame, the rotatable platform being rotatable about a first rotational axis; and
a turntable comprising:
a stage platform for holding a component having an area of interest, the area of interest having a rotational axis; and
a mounting plate for engagement with the rotatable platform, the mounting plate rotating with the rotatable platform about the first rotational axis;
wherein the stage platform is moveable in a first direction from a starting position to an imaging position, the first direction being perpendicular to the first rotational axis.

2. The component imaging system of claim 1, configured such that in the imaging position, the rotational axis of the area of interest is aligned with the first rotational axis.

3. The component imaging system of claim 1, further comprising a controller for controlling movement of the stage platform from the starting position to the imaging position.

4. The component imaging system of claim 3, further comprising a first rail assembly connected to the stage platform, the first rail assembly comprising:
a rail;
a guide slidably connected to the rail; and
a motor for actuating movement of the guide relative to the rail.

5. The component imaging system of claim 4, further comprising:
a first set of contacts on the mounting plate of the turntable, the first set of contacts in electrical communication with the motor of the first rail assembly; and
electrical leads for electrical communication with the controller, the electrical leads fixedly positioned relative to the rotatable platform.

6. The component imaging system of claim 5, wherein when the first set of contacts are in electrical communication with the electrical leads, an electrical signal is permitted to be provided to the motor to actuate movement of the guide relative to the rail to move the stage platform in the first direction.

7. The component imaging system of claim 6, further comprising a second rail assembly connected to the first rail assembly, the second rail assembly comprising:
a rail;
a guide slidably connected to the rail; and
a motor for actuating movement of the guide relative to the rail.

8. The component imaging system of claim 7, wherein the second rail assembly is connected to the first rail assembly such that the rail of the second rail assembly is perpendicular the rail of the first rail assembly.

9. The component imaging system of claim 7, further comprising a second set of contacts on the mounting plate of the turntable, the second set of contacts in electrical communication with the motor of the second rail assembly.

10. The component imaging system of claim 9, wherein the second set of contacts is positioned on the mounting table about 90 degrees apart from the first set of contacts.

11. The component imaging system of claim 10, wherein when the second set of contacts are in electrical communication with the electrical leads, an electrical signal is provided to the motor of the second rail assembly to actuate movement of the guide of the second rail assembly relative to the rail of the second rail assembly to move the stage platform in a linear direction that is nonparallel with the first direction.

12. The component imaging system of claim 1, further comprising a platform track assembly, wherein the rotatable platform is mounted to the track assembly for linear movement of the rotatable platform.

13. The component imaging system of claim 12, further comprising a base track assembly extending between the first end and the second end of the frame.

14. The component imaging system of claim 13, wherein the platform track assembly is connected to the base track assembly for linear movement of the rotatable platform relative to the first end and the second end.

15. A manipulator for a component imaging system, the manipulator comprising:
   a mounting plate rotatable about a first rotational axis from a first position to a second position; and
   a stage platform having a surface for holding a component having an area of interest to be imaged, the stage platform having a center and a central axis perpendicular to the surface and running through the center;
   wherein the stage platform is rotatable about the first rotational axis with the mounting plate, and the stage platform is moveable radially relative to the mounting plate from an initial position to an imaging position, wherein in the imaging position the central axis is unaligned with the first rotational axis.

16. The manipulator of claim 15, further comprising a first rail assembly for radially moving the stage platform.

17. The manipulator of claim 16, further comprising a controller configured for selectable electrical communication with the first rail assembly.

18. The manipulator of claim 17, wherein when the controller is in electrical communication with the first rail assembly, the controller is permitted to send a signal to a motor of the first rail assembly to move the stage platform along the rail assembly.

19. The manipulator of claim 17, further comprising two sets of contacts and the controller is configured for selectable electrical communication between the two sets of contacts.

20. The manipulator of claim 19, further comprising a second rail assembly for radially moving the stage platform in a direction different than provided by the first rail assembly, wherein the first rail assembly is in electrical communication with a first set of the two sets of contacts and the second rail assembly is in electrical communication with a second set of the two sets of contacts.

* * * * *